United States Statutory Invention Registration [19]

[11] Reg. Number: H602

Terashima

[43] Published: Mar. 7, 1989

[54] WHOLE BLOOD DILUTING SOLUTION

[76] Inventor: Masaaki Terashima, c/o Fuji Photo Film Co., Ltd., No. 11-46, Senzui 3-chome, Asaka-shi, Saitama, Japan

[21] Appl. No.: 97,624

[22] Filed: Sep. 16, 1987

[30] Foreign Application Priority Data

Sep. 16, 1986 [JP] Japan ..... 61-217634

[51] Int. Cl.[4] ..... G01N 31/00; G01N 21/77

[52] U.S. Cl. ..... 436/18; 436/95; 436/169

*Primary Examiner*—John F. Terapane
*Assistant Examiner*—Susan Wolffe
*Attorney, Agent, or Firm*—Jules E. Goldberg

[57] ABSTRACT

A whole blood diluting solution for analyzing quantitatively whole blood (even when it contains a subject component in an abnormally high quantity, or it is used as a sample after a several-hour hapse from blood-gathering) by supplying a given volume of whole blood sample in the form of a diluted solution to a dry analysis material, which has at least one porous layer side, with the diluting solution containing a water-insoluble dispersed phase (made up of, e.g., macromolecular substances), preferably in an emulsified or suspended condition isotonic to whole blood.

13 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

WHOLE BLOOD DILUTING SOLUTION

BACKGROUND OF THE INVENTION

1. Field of the Invention

The present invention relates to a diluting solution for diluting a whole blood sample, if needed, in analyzing a target component or analyte in the quantitative analysis contained in the whole blood sample, using an element for dry analysis. More particularly, it is concerned with a diluting solution and an analytical process using said diluting solution for the quantitative analysis of diluted whole blood samples using, for example, analysis element comprising paper impregnated with a color-producing reagent, or a multilayer analysis element comprising a light-permeable, water-impermeable support having at least one reagent layer and an outermost porous layer.

2. Description of the Prior Art

Dry analysis materials or elements and methods for analyzing quantitatively aqueous liquid samples using them are described in U.S. Pat. Nos. 3,552,928, 3,368,872, 3,036,893, 3,016,292 and 2,846,808, and so on.

Multilayer dry analysis elements comprising a transparent support having thereon at least one reagent layer and a porous layer, in this order, and quantitative analysis methods of aqueous liquid samples using those materials are described, e.g., in, Japanese Patent Application (OPI) Nos. 53888/74 137192/75, 140191/76, 3488/77, 131089/78, 101398/79, 90859/80, 164356/80, 24576/81, etc. (as used herein "OPI" means an "unexamined published application"), H. G. Curme et al and R. W. Spayd et al., *Clinical Chemistry,* vol. 24, pp. 1335–1350 (1978), Bert Walter, *Anal. Chem.,* vol. 55, No. 4, pp. 498–514, and so on. These references describe the possibility of using non-diluted serum, blood plasma and diluted whole blood as a sample.

More specifically, examples of a clinical test to determine blood glucose using non-diluted whole blood as a sample and a multilayer analysis element as the analysis means are described in Ohkubo et al., *Clinical Chemistry,* vol. 27, pp. 1287–1290 (1981).

In the clinical application of the whole blood sample analysis using a multilayer dry analysis material, satisfactory analysis results were obtained when fresh whole blood having normal ranges for the hematocrit value and fluidity was employed as a sample. However, it was found that substantial lowering of precision and accuracy of the analysis results occurred frequently when whole blood containing a component to be analyzed in an abnormally high content, having an abnormally high hematocrit value, or having low fluidity was employed as a sample, or whole blood was used as a sample after a several-hour lapse from blood sampling. The above problems did not occur for blood serum or blood plasma, even when the dry analysis method was used. However, rapidity and simplicity of the dry analysis method are lost, since the sample must be centrifuged to obtain blood serum or blood plasma. In determining an analyte in blood, there is much need of obtaining the result of analysis simply and immediately using the whole blood as it is, as a sample, and a dry analysis element as an analyzing implement.

When whole blood containing a component to be analyzed in an abnormally high concentration, whole blood having an abnormally high hematocrit value, or whole blood having low fluidity is handled, it is conventional to dilute the whole blood with an appropriate aqueous diluting solution. When whole blood is diluted, it is desirable that the diluting solution should be a solution having, substantially no hemolytic function, and further, does not cause agglutination of red corpuscles by dilution so that no change in fluidity of the whole blood sample occurs. As for the aqueous diluting solutions having the above characteristics, isotonic solutions containing inorganic salts, such as, physiological saline (including physiological salt solution, Ringer's solution, etc.), and isotonic solutions having a viscosity adjusted properly by addition of a hydrophilic or water-soluble organic substance, such as dextran, polyvinyl pyrrolidone, albumin, etc., to physiological saline have generally been employed. However, whole blood samples diluted with these aqueous diluting solutions exhibit responses different from their neat whole blood samples with respect to, e.g., color development of an analyte applied to a dry analysis element. That is, the analyte concentration calculated by multiplying the concentration derived from the calibration curve determined using neat whole blood samples, by the dilution factor, is not exact. The concentration-dilution factor relationship to correct the above-described error is so complicated that the dilution with the isotonic solutions described above is impractical.

SUMMARY OF THE INVENTION

An object of the present invention is to provide a diluting solution which can produce satisfactory results in quantitative analyses using a dry analysis element of not only normal whole blood but also abnormal blood, wherein the blood sample is diluted to a definite volume with said diluting solution. It is a further object of the present invention is to extend an applicable scope of dry analysis elements to whole blood samples, particularly, to abnormal whole blood samples.

More specifically, the object of the present invention is to achieve analytical precision and accuracy equivalent to those attainable for normal whole blood samples, by dilution with a diluting solution of a gathered sample, in the case where the sample to be analyzed is (1) a whole blood sample which contains a subject component of analysis in an amount beyond the upper limit of measurable range,
(2) a whole blood sample having an abnormally high hematocrit value,
(3) a whole blood sample having a low fluidity, or
(4) a whole blood sample which has been allowed to stand for several hours or longer after blood-sampling.

In accordance with the invention, the above-described objects are attained by using as the whole blood diluting solution, a diluting solution containing a water-insoluble dispersed phase.

BRIEF DESCRIPTION OF THE DRAWINGS

(In FIGS. 3 and 4, triangular marks (Δ) designates data of whole blood samples having a hematocrit value of 20%, square marks (□) designates those having a hematocrit value of 40%, and round marks (O) those having a hematocrit value of 60%.)

FIG. 4 is a correlation graph obtained by plotting the Glucoroder value against the whole blood (undiluted) value of Table 1.

DETAILED DESCRIPTION OF THE INVENTION

Figure 1:
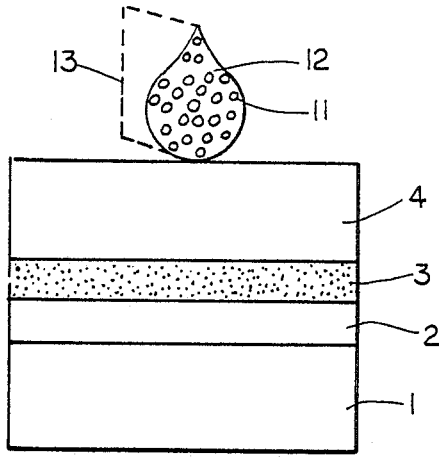
FIG. 1 and FIG. 2 are schematic diagrams for illustrating a method of analyzing a whole blood sample using a multilayer film for dry analysis.

Referring to FIG. 1, a method of whole blood analysis using a multilayer analysis element is illustrated schematically. The exemplified multilayer analysis element is an analysis film having a multilayer structure provided with a reagent layer 2, light-reflecting layer 3 and a porous spreading layer 4 on one side of a transparent support 1 (wherein, of course, plural reagent layers, a barrier layer, a scavenger layer, a buffer layer, a detector and so on may be interposed between the support and the spreading layer, if needed). When a whole blood sample 13 having a concrete or filtrable component 11 and a liquid component 12 in the form of a spot is put on the porous spreading layer 4 of a multilayer analysis film, the whole blood spreads rapidly in a circle over the porous spreading layer. The area of the circle is approximately proportional to the quantity of sample put thereon. The liquid component then passes through the porous spreading layer as the concrete component is filtered out, and successively passses through the light-reflecting layer 3 and arrives at the reagent layer 2. In principle, a selective colorproducing reagent capable of reacting only with an analyte in the blood is incorporated in the reagent layer in advance, so that color development takes place in proportion to the content of the analyte. The optical density of the color in the color-developed region 14 is measured with a colorimeter from the support side, and the content of the analyte in the blood can be determined by colorimetry.

The porous spreading layer 4 is made up of a material selected from among membrane filter-form nonfibrous isotropic porous materials, porous materials made of powdery granules, textiles, paper, and so on. The spreading layer is capable of a metering or spreading function such that when a drop of aqueous liquid sample is placed thereon, the aqueous liquid spreads rapidly in a circle in the horizontal direction and then penetrates in vertical direction, and the aqueous liquid is supplied to the reagent layer located thereunder in an approximately constant volume per unit area. In particular, using a textile having a construction made up of fine granules and containing continuous vacant spaces therein, as described in Japanese Patent Application (OPI) No. 90859/80, and the like, enables the quantitive analysis of whole blood, because those materials possess a spreading function with a respect to not only blood plasma and serum, but also, whole blood containing a concrete component.

A whole blood diluting solution to be used in the present invention, which contains a water-insoluble dispersed phase, is described in detail below.

Figure 2:
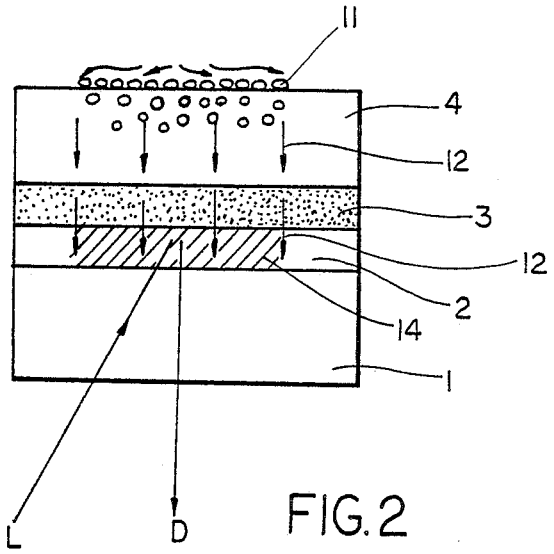

FIG. 2 illustrates schematically the phenomenon wherein a concrete component in the whole blood sample (e.g., red blood corpuscles) is filtered out by the porous spreading layer to remain on the surface and the inner part near the surface of the spreading layer, while a liquid component is spreaded by passing through the spreading layer, and further passes through the light-reflecting layer, and reaches the reagent layer.

When the water-insoluble dispersed phase is a solid phase, it can be made up of a substance selected from a group consisting of styrene homopolymer, copolymers prepared from styrene and monomers copolymerizable with styrene, acrylate homopolymers, copolymers prepared from acrylates and monomers copolymerizable with acrylates, vinyl acetate homopolymer, copolymers prepared from vinyl acetate and monomers copolymerizable with vinyl acetate, vinyl chloride homopolymer, copolymers prepared from vinyl chloride and monomers copolymerizable with vinyl chloride, red blood corpuscles, and ghosts of red blood corpuscles.

When the water-insoluble dispersed phase is a polymer or a copolymer, the molecular weight thereof ranges preferably from $1\times10^4$ to $1\times10^6$. Preferable monomer copolymerizable with styrene, acrylate, vinyl acetate, or vinyl chloride described above is at least one monomer selected from the group consisting of acrylic acid, acrylonitrile, acrylamide, ethylene and maleic acid.

When the water-insoluble dispersed phase is a liquid phase, it can be made up of a substance selected from a group consisting of adipates, sebacates, trimellitates and phosphates. Details of these substances are disclosed in Japanese Patent Application (OPI) No. 122956/81.

The alcohol moiety composing the above esters preferably includes a straight or branched alcohol having from 4 to 10 carbon atoms.

The diluting solution contains preferably from 10 to 50 wt %, more preferably from 15 to 30 wt % of the water-insoluble dispersed phase.

The undiluted whole blood sample may be diluted to preferably from 2 to 10 times, more preferably from 3 to 5 times by volume, using the diluting solution.

The above-described water-insoluble dispersed phase is an emulsion or a suspension having a particle size which ranges from 0.01 micron to 10 microns. So long as the phase to be dispersed can be mixed homogeneously with a water phase by a simple stirring operation, the phase may be employed in the present invention, Thus, the dispersed phase is not always required to be a stable dispersion. However, it is more desirable that the dispersed phase assumes the form of stable suspension or emulsion. Optionally, known additive, such as, surface active substances, defoaming agents, antiseptics, etc. can be added to the aqueous diluting solution so long as the addition does not cause interference with the intended analyses. Organic solvents which can be used in the invention include alcohols, such as, methanol, ethanol, benzyl alcohol, etc. Other organic liquid substances can be also added to the aqueous diluting solution.

As suitable examples of antiseptics, mention may be made of parachlorophenol derivatives and benzothiazole derivatives as described in Japanese Patent Application Nos. 58765/86 and 89348/86.

In addition, a glycolysis inhibitor, agglutination inhibitor and like additives are generally added to whole blood taken from a human or animal body immediately after blood sampling, except when the sampled whole blood is immediately subjected to analysis.

Dilution can be carried out by (1) adding an aqueous diluting solution to whole blood, (2) adding whole blood to an aqueous diluting solution, or (3) pouring both whole blood and an aqueous diluting solution almost simultaneously into a third vessel. After the whole blood and the aqueous diluting solution are combined, the resulting mixture is preferably submitted to gentle stirring or shaking in order to form a homogeneous mixture of the aqueous diluting solution with the plasma component in the whole blood, and particularly, the concrete component in the whole blood. For the purpose of simplifying a diluting operation of whole blood, it is possible, for example, to suck up a desired volume of aqueous diluting solution with a droplet forming instrument, such as, a micropipette, and subsequently to suck up a definite volume of whole blood with the same micropipette to produce a mixture of the components. When the dilution is carried out in the described manner, one can readily proceed to placing the diluted whoe blood in a drop on the porous spreading layer as described hereinafter.

In accordance with the operation techniques described in the above-cited patent specifications and literatures, a drop of diluted whole blood sample is then placed on the porous spreading layer of a dry analysis material and incubated, if necessary. The optical density of the color developed area is measured by a reflex photometry, and a content of the analyte in the whole blood sample is determined according to the principle of the colorimetric method. Also, it is possible to carry out the photometry of the color-developed area of the dry analysis material using a fluorometric technique. The analyte content in the diluted whole blood sample is determined first. Since the analyte content in the diluted whole blood sample is determined at once by measuring the optical density of the color-developed region and using the same calibration curve obtained from the undiluted whole blood sample, analyte content in the undiluted whole blood sample can be determined only by multiplication of the content in the diluted sample by the dilution factor. When the dilution factor is set for 2, 3, 4 or 5, the multiplication becomes very easy.

The hematocrit value of whole blood varies widely with the individual and therefore, a proportion of the volume occupied by blood plasma in whole blood fluctuates widely depending on the hematocrit value, too. Nevertheless, an analyte content in the undiluted whole blood sample can be derived from the analyte content in the diluted whole blood sample by using only the entire volume of the whole blood sample and the dilution factor which is a remarkable characteristic of the method of the present invention. In addition, application of the whole blood diluting solution of the present invention is not confined to materials for dry colorimetric analysis. It is also possible to apply it to analysis methods which treat whole blood as a sample and use a chemical sensor utilizing an oxygen electrode, a carbon dioxide electrode, a pH electrode, an enzyme electrode, a filed effect transistor (FET) or so on.

The present invention is illustrated in more detail by reference to the following example.

EXAMPLE 1

The glucose concentration in whole blood was determined in the following manner, in which a diluting solution for diluting whole blood and a quantitative multilayer analysis film for glucose were employed.

Fresh human blood to which heparin was added immediately after blood-gathering was centrifuged to separate it into a plasma component and a corpuscle component. These two components were taken out of the apparatus separately, and then mixed in various ratios to reprepare whole blood samples having hematocrit values within the range of 20% to 60%. Further, glucose was added and dissolved into each whole blood sample in an amount necessary to adjust the glucose concentration to about 100 to 1600 mg/dl. Thus, 30 kinds of whole blood samples as shown in Table 1, which differed in hematocrit value and glucose concentration, were prepared.

Separately, a basic solution for an aqueous diluting solution, which had the following composition, was prepared.

| Composition of Basic Solution for Aqueous Diluting Solution | |
|---|---|
| NaCl | 9 g |
| Distilled Water | 360 g |
| Cebian A* | 640 g |
| Suraofu 72N** | 0.2 g |

* Products of Daicel Ltd. (Copolymer of styrene and ethylacrylate (1:4 molar ratio), molecular weight: about $1 \times 10^5$, solid content: 30 wt %, average particle diameter: 0.3 μ)

** antiseptics produced by Takeda Chemical Industries Ltd.

A diluted whole blood sample was prepared by adding 300 microliter of the aqueous diluting solution to 100 microliter of the above-described whole blood sample to dilute the whole blood sample exactly 4 times by volume ratio.

Further, a slide for dry chemical analysis of glucose was made in the following manner.

On a 180 μm-thick smooth film of polyethylene terephthalate having an undercoat of gelatin, a coating solution for forming a reagent layer, which had the following composition, was coated so as to have a dry thickness of 15 microns, and dried.

| | |
|---|---|
| Gelatin | 20 g |
| Peroxidase | 2500 IU |
| Glucose Oxidase | 1000 IU |
| 1,7-Dihydroxynaphthalene | 0.5 g |
| 4-Aminoantipyrine | 0.5 g |
| Polyoxyethylene Nonylphenol | 0.2 g |
| Water | 200 ml |

On the reagent layer, was coated a coating solution for forming a light shielding layer, which had the following position, so as to have a dry thickness of 7 microns, and dried.

| | |
|---|---|
| Gelatin | 10 g |
| Titanium Dioxide | 100 g |
| Water | 500 ml |

On the light shielding layer, an adhesive layer having the following composition was coated so as to have a dry thickness of 2 μm, and dried.

| | |
|---|---|
| Gelatin | 4 g |
| Polyoxyethylene Nonylphenol | 0.1 g |
| Water | 200 ml |

The adhesive layer was moistened with water in a quantity of 30 g/m$^2$, and cotton broadcloth was adhered to it by applying light pressure thereon, followed by drying.

The glucose analyzing film made in the above-described manner was cut into pieces measuring 15 mm ×15 mm in size, and each piece was put on a thermoplastic resin flame measuring 24 mm by 28 mm in size.

As for the 30 kinds of whole blood samples and the 30 kinds of diluted whole blood samples, a six micro liter portion was collected from each sample with a micropipette, a droplet of each was placed on the developing layer of the above-described analysis slide, and then incubated at 37° C. for 6 minutes. Thereafter, the glucose concentration was determined using the optical reflection density measured on the PET film side with a photometer using a colorimetric method. The data obtained are set forth in the third and forth columns of Table 1. The values calculated by multiplying the glucose concentrations in the diluted whole blood samples by 4, which are to be used as those of undiluted samples, are set forth in the extreme right column.

On the other hand, each whole blood sample was centrifuged, and the resulting blood plasma was examined for glucose concentration using a Glucoroder (made by Shino Test Co., Ltd.), or a glucose analyzer based on an enzyme electrode process. The results obtained are set forth at the second column from the left. The term Hct in the table refers to a hematocrit value.

TABLE 1

| | Glucoroder Data | Whole Blood Sample (undiluted) | Whole Blood Sample diluted 4 times (A) | A × 4 |
|---|---|---|---|---|
| Hct 20 | | | | |
| 1 | 63 | 69 | 20 | 80 |
| 2 | 165 | 164 | 48 | 192 |
| 3 | 263 | 222 | 62 | 248 |
| 4 | 441 | 421 | 111 | 444 |
| 5 | 582 | 600 | 151 | 604 |
| 6 | 764 | impossible to measure | 191 | 764 |
| 7 | 924 | " | 240 | 960 |
| 8 | 1146 | " | 290 | 1160 |
| 9 | 1290 | " | 313 | 1252 |
| 10 | 1422 | " | 334 | 1336 |
| Hct 40 | | | | |
| 11 | 120 | 130 | 27 | 108 |
| 12 | 222 | 222 | 56 | 224 |
| 13 | 327 | 322 | 91 | 364 |
| 14 | 531 | 506 | 128 | 512 |
| 15 | 735 | 540 | 180 | 720 |
| 16 | 933 | 548 | 239 | 956 |
| 17 | 1149 | 544 | 302 | 1208 |
| 18 | 1308 | 513 | 323 | 1292 |
| 19 | 1530 | 525 | 367 | 1468 |
| 20 | 1623 | 489 | 397 | 1588 |
| Hct 60 | | | | |
| 21 | 75 | 75 | 23 | 92 |
| 22 | 192 | 190 | 50 | 200 |
| 23 | 264 | 259 | 70 | 280 |
| 24 | 480 | 344 | 120 | 480 |
| 25 | 684 | 363 | 171 | 684 |
| 26 | 903 | 350 | 222 | 888 |
| 27 | 1002 | 363 | 236 | 944 |
| 28 | 1347 | 347 | 321 | 1284 |
| 29 | 1400 | 375 | 341 | 1364 |
| 30 | 1647 | 373 | 403 | 1612 |

Figure 3:
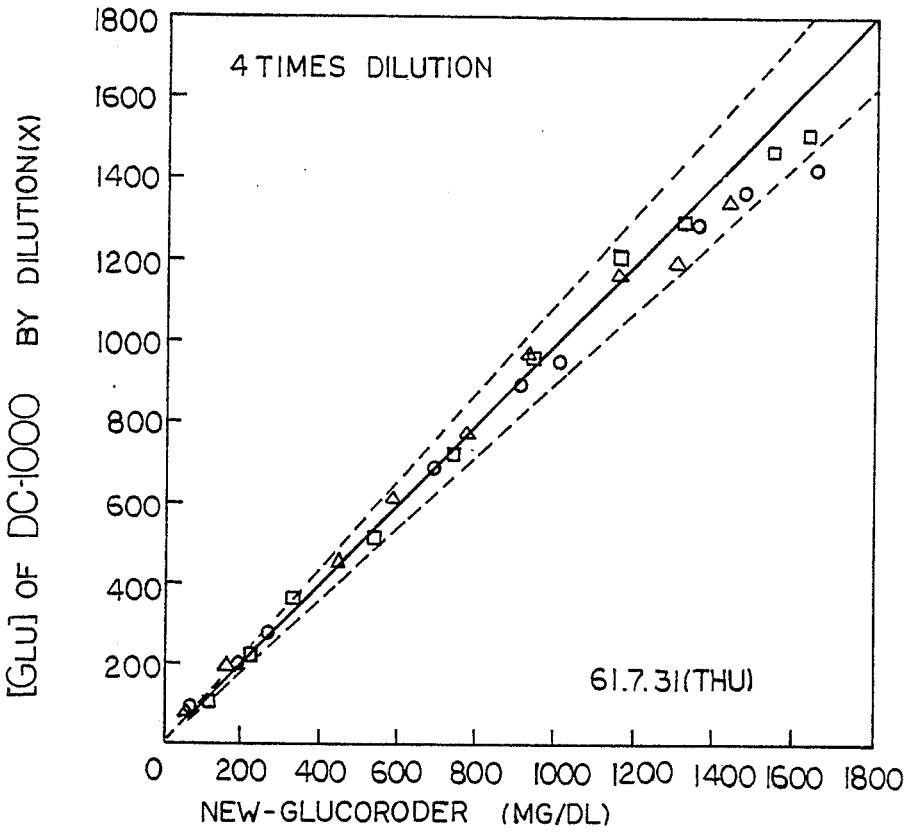
FIG. 3 is a correlation graph obtained by plotting the dGlucoroder values against the (A×4) values of Table 1.
Figure 4:
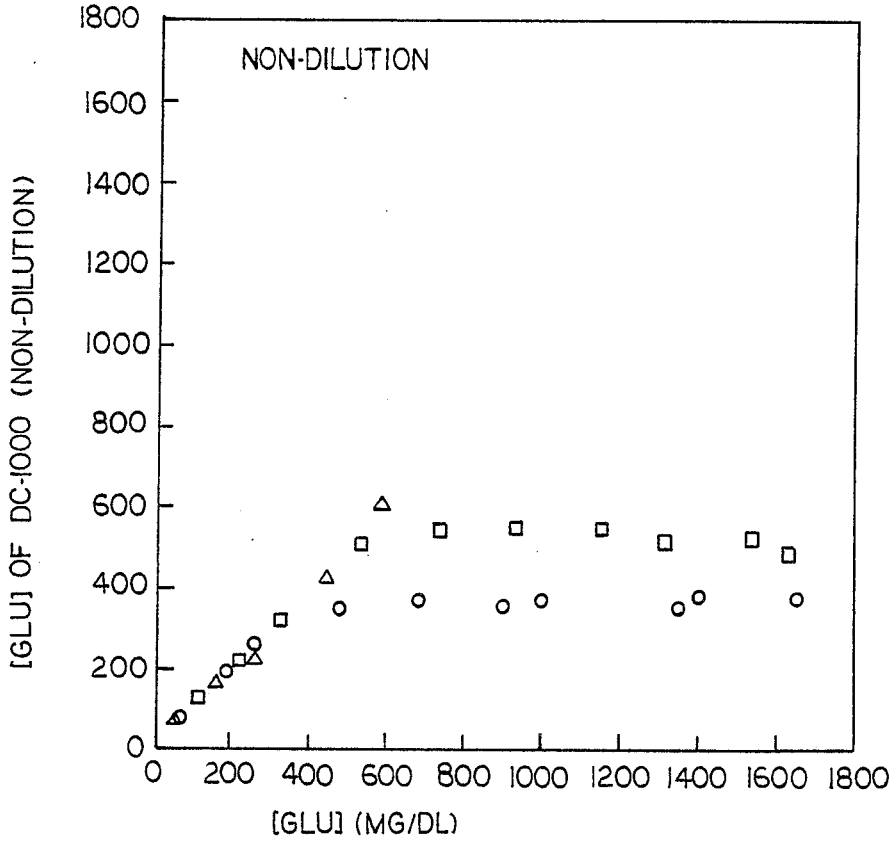

As can be seen from the data in Table 1, and as depicted in FIG. 4, the conventional method in which glucose concentration is determined through putting a drop of undiluted whole blood sample on a multilayer material for dry analysis has a tendency to produce glucose concentration values lower than those obtained by a Glucoroder based on an enzyme electrode process. This latter method has been prevailingly used for measurement of glucose concentration in blood when whole blood samples having high glucose concentrations are analyzed. This tendency becomes more pronounced as the hematocrit value becomes higher. In contrast to the conventional method, the glucose concentration value determined with the method of the present invention in which a whole blood sample, diluted 4 times with the whole blood diluting solution of the present invention, is put in droplet form on a multilayer material for dry analysis provided data, agree well with those obtained by the enzyme electrode process even in the high glucose concentration region and further in the high hematocrit value region, as is apparent from FIG. 3.

While the invention has been described in detail and with reference to specific embodiments thereof, it will be apparent to one skilled in the art that various changes and modifications can be made therein without departing from the spirit and scope thereof.

What is claimed is:

1. A whole blood diluting solution for use in analyzing whole blood quantitatively by applying a given volume of a whole blood sample in the form of diluted solution to an element for dry analysis having at least one porous layer and containing at least one reagent onto the porous layer side, said diluting solution containing a dispersed phase insoluble in water.

2. The whole blood sample diluting solution of claim 1 wherein the particle size of said dispersed phase insoluble in water ranges from 0.01 micron to 10 microns.

3. The whole blood sample diluting solution of claim 1 wherein said dispersed phase insoluble in water is contained in a proportion of from 10 to 50%.

4. The whole blood sample diluting solution of claim 1, wherein said dispersed phase insoluble in water is made up of a macromolecular substance selected form the group consisting of styrene homopolymer, copolymers prepared from styrene and monomers capable of copolymerizing with styrene, acrylate homopolymers, copolymers prepared from acrylates and monomers capable of copolymerizing with acrylates, vinyl acetate homopolymers, copolymers prepared from vinyl acetate and monomers capable of copolymerizing with vinyl acetate, vinyl chloride homopolymers, copolymers prepared from vinyl chloride and monomers capable of copolymerizing with vinyl chloride, red blood corpuscles, and ghosts of red blood corpuscles.

5. The whole blood sample diluting solution of claim 1 wherein said water-insoluble, dispersed phase is a suspension or an emulsion.

6. The whole blood sample diluting solution of claim 1 which is substantially isotonic to whole blood.

7. In a method of analyzing quantitatively a particular analyte in a whole blood sample by the use of a dry analysis element having at least one reagent layer and a porous layer in fluid contact with the reagent layer wherein the sample containing the analyte is placed onto the porous layer, the improvement which comprises diluting the whole blood sample with a diluting solution containing a dispersed phase insoluble in water.

8. The method of claim 7 wherein said analyte is glucose.

9. The method of claim 7 wherein the particle size of said dispersed phase insoluble in water ranges from 0.01 micron to 10 microns.

10. The method of claim 7 wherein said dispersed phase insoluble in water is contained in a proportion of from 10 to 50%.

11. The method of claim 7 wherein said dispersed phase insoluble in water is made up of a macromolecular substance selected from the group consisting of styrene homopolymer, copolymers prepared from styrene and monomers capable of copolymerizing with styrene, acrylate homopolymers, copolymers prepared from acrylates and monomers capable of copolymerizing with acrylates, vinyl acetate homopolymers, copolymers prepared from vinyl acetate and monomers capable of copolymerizing with vinyl acetate, vinyl chloride homopolymers, copolymers prepared from vinyl chloride and monomers capable of copolymerizing with vinyl chloride, red blood corpuscles, and ghosts of red blood corpuscles.

12. The method of claim 7 wherein said water-insoluble, dispersed phase is a suspension or an emulsion.

13. The method of claim 7 wherein the diluting solution is substantially isotonic to whole blood.

* * * * *